United States Patent [19]

Mizutani et al.

[11] Patent Number: 5,504,128
[45] Date of Patent: Apr. 2, 1996

[54] THERMOPLASTIC RESIN COMPOSITION AND A METHOD OF MOLDING THE SAME

[75] Inventors: Toshihiro Mizutani, Yawata; Kango Fujitani; Mikio Nakazawa, both of Uji, all of Japan

[73] Assignee: New Japan Chemical Co., Ltd., Kyoto, Japan

[21] Appl. No.: 387,806
[22] PCT Filed: Jun. 28, 1994
[86] PCT No.: PCT/JP94/01035
§ 371 Date: Feb. 21, 1995
§ 102(e) Date: Feb. 21, 1995
[87] PCT Pub. No.: WO95/01393
PCT Pub. Date: Jan. 12, 1995

[30] Foreign Application Priority Data

Jun. 30, 1993 [JP] Japan .................................. 5-188726
Apr. 6, 1994 [JP] Japan .................................. 6-093765

[51] Int. Cl.$^6$ ...................... C07D 207/40; C08K 5/3415
[52] U.S. Cl. ............................ 524/104; 524/105; 548/520
[58] Field of Search ............... 264/239; 524/104, 524/105; 548/520

[56] References Cited

U.S. PATENT DOCUMENTS

| | | | |
|---|---|---|---|
| 3,182,072 | 5/1965 | Ladd ........................................ | 524/105 |
| 3,491,057 | 1/1970 | Kato et al. ............................... | 524/104 |
| 3,520,847 | 7/1970 | Runge et al. ............................ | 524/104 |
| 3,790,597 | 2/1974 | Dexter et al. ........................... | 524/105 |
| 3,887,582 | 6/1975 | Holub et al. ............................. | 524/104 |
| 4,078,091 | 3/1978 | Dale et al. .............................. | 524/105 |
| 4,346,188 | 8/1982 | Costanzi et al. ........................ | 524/104 |

*Primary Examiner*—Kriellion S. Morgan
*Attorney, Agent, or Firm*—Larson & Taylor

[57] ABSTRACT

This invention provides a thermoplastic resin composition comprising a thermoplastic resin and 0.1 to 100 parts by weight, per 100 parts by weight of the thermoplastic resin, of an imide compound prepared, e.g., by dehydration condensation of 1,2,3,4-butanetetracarboxylic acid or a monoanhydride or a dianhydride thereof with a primary amine, and a method of molding the resin composition.

26 Claims, No Drawings

THERMOPLASTIC RESIN COMPOSITION AND A METHOD OF MOLDING THE SAME

TECHNICAL FIELD

The present invention relates to a thermoplastic resin composition and a method of molding the composition.

TECHNICAL BACKGROUND

Recently heat-resistant thermoplastic resins have been used as engineering plastics for machine materials or electronic parts. In molding a thermoplastic resin, in order to improve productivity, it has been proposed to blend, for the purpose of reducing melt viscosity, promoting crystallization and improving mold releasability, various resin modifiers, e.g., fatty acids such as stearic acid, metal salts of fatty acids, ester derivatives prepared from a fatty acid with a polyhydric alcohol such as pentaerythritol, polyethylene glycol or the like, aliphatic amides such as ethylenebisstearamide, etc. (Japanese Unexamined Patent Publications (Kokai) No. 44547/1985 and No. 250049/1991).

However, since heat-resistant thermoplastic resins generally have a high fusing temperature, said resin additives may thermally decompose or boil when melted, thereby tending to stain a mold or form void in the resin. For this reason, it has been desired to develop heat-resistant resin modifiers.

In view of the recent increasing need for plastic materials of high performance, polyarylene sulfide (PAS) excellent in heat resistance, mechanical characteristics and chemical resistance is attracting attention, and is now used for extending applications, for example, as automotive parts, parts for precision machines, electric and electronic parts, etc.

PAS is a crystalline engineering plastic but has low crystallization rate. Therefore, in order to obtain a resin of sufficient mechanical strength by injection molding, a high mold temperature of about 130° C. and a prolonged cooling time were necessary. This defect posed a serious problem in extending the applications of PAS, and it is desired to mold PAS in a short time at a mold temperature of not higher than 100° C. which is among the molding conditions for resin-molding apparatus commonly used.

To solve this problem, there have been proposed a method of increasing the mold releasability by adding a fatty acid ester (Japanese Unexamined Patent Publication No.154867/1992), an aromatic sulfonamide (Japanese Unexamined Patent Publication No.59279/1993) or the like, and a method of promoting the crystallization by adding a modified polyalkylene glycol (Japanese Unexamined Patent Publication No.250049/1991) or an organic phosphoric acid metal salt (Japanese Unexamined Patent Publication No.142854/1990) or the like.

However, because of insufficient heat resistance of the resulting resin compositions, these methods entail the problem of failing to achieve the contemplated results and the problem of exhibiting reduced mechanical strength and heat resistance even if the mold releasability or appearance of the molded products may be improved.

DISCLOSURE OF THE INVENTION

An object of the present invention is to provide a novel and useful thermoplastic resin composition containing a resin modifier which is excellent in heat resistance.

Another object of the invention is to provide a novel and useful method of molding a thermoplastic resin composition, which method is feasible even at a low temperature without deteriorating the inherent mechanical characteristics and heat resistance of the thermoplastic resin, particularly polyarylene sulfide.

The inventors of the present invention conducted extensive research to solve the foregoing problems, and found that an imide compound having a specific structure can function as a resin modifier having the desired performance since the imide compound per se has high heat resistance and reduces the melt viscosity of thermoplastic resins, increases the crystallizability of crystalline thermoplastic resins or enhances the mold releasability, etc. The present invention has been accomplished based on these novel findings.

The present inventors further found that when a thermoplastic resin composition, particularly a polyarylene sulfide resin composition, containing the above specific imide compound is used, a molded article which retains the inherent mechanical strength and heat resistance of the thermoplastic resins, especially of the polyarylene sulfide, can be obtained even at a mold temperature of 100° C. or lower.

Thus, the thermoplastic resin composition according to the present invention is characterized in that the composition comprises a thermoplastic resin and 0.1 to 100 parts by weight, per 100 parts by weight of said thermoplastic resin, of an imide compound, said imide compound being at least one member selected from the group consisting of:

(1) a bisimide represented by the formula

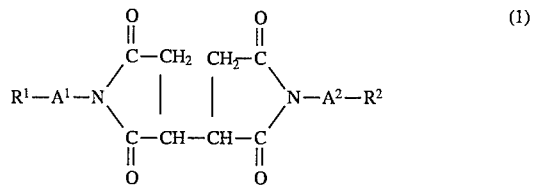

wherein $R^1$ and $R^2$ are the same or different and each represents an alkyl or alkenyl group having 4 to 22 carbon atoms, a cycloalkyl group having 4 to 6 carbon atoms a group represented by the formula

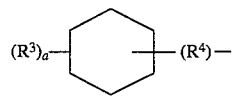

or a group represented by the formula

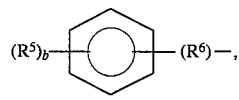

in which $R^3$ and $R^5$ are the same or different and each represents an alkyl group having 1 to 22 carbon atoms, $R^4$ and $R^6$ are the same or different and each represents a single bond or an alkylene group having 1 to 2 carbon atoms, a is an integer of 1 to 2 and b is an integer of 0 to 2, and $A^1$ and $A^2$ are the same or different and each represents a single bond or a phenylene group;

(2) a monoimide represented by the formula

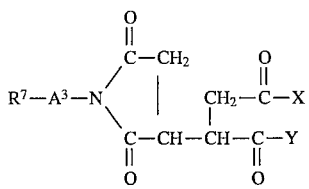

wherein X and Y are the same or different and each represents a group of the formula —NH—$A^4$—$R^8$ or a hydroxyl group, $R^7$ and $R^8$ have the same meaning as $R^1$ in the formula (1) and may be the same or different, and $A^3$ and $A^4$ are the same or different and each represents a single bond or a phenylene group, and a metal salt thereof; and (3) a monoimide represented by the formula

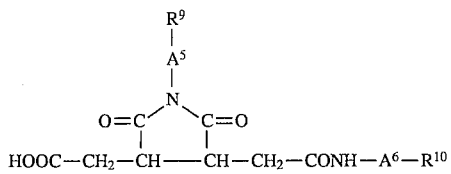

wherein $R^9$ and $R^{10}$ are the same or different and each represents an alkyl or alkenyl group having 4 to 22 carbon atoms, and $A^5$ and $A^6$ are the same or different and each represents a single bond or a phenylene group, and a metal salt thereof.

The present invention also provides a method of molding a thermoplastic resin composition, particularly a polyarylene sulfide resin composition, the method being characterized in that the method comprises injection-molding or blow-molding a resin composition comprising a thermoplastic resin, particularly a polyarylene sulfide resin, and 0.1 to 100 parts by weight, per 100 parts by weight of said thermoplastic resin, of at least one imide compound selected from the group consisting of a bisimide of the formula (1), a monoimide of the formula (2) and a metal salt thereof and a monoimide of the formula (3) and a metal salt thereof.

The imide compounds of the formulas (1), (2) and (3) for use in the invention can be easily prepared, for example, by dehydration condensation of 1,2,3,4-butanetetracarboxylic acid (hereinafter referred to as "BTC") or a monoanhydride or dianhydride thereof (BTC and a monoanhydride or dianhydride thereof will be hereinafter collectively referred to as "BTC compound") with an aliphatic primary amine, an alicyclic primary amine or an aromatic primary amine represented by the formula $H_2N$—$A^1$—$R^1$, $H_2N$—$A^2$—$R^2$, $H_2N$—$A^3$—$R^7$, $H_2N$—$A^4$—$R^8$, $H_2N$—$A^5$—$R^9$ or $H_2N$—$A^6$—$R^{10}$, or alternatively by decarboxylation reaction of said BTC compound with an isocyanate derivative corresponding to said amine (stated more specifically, a compound of the formula O=C=N—$A^1$—$R^1$, O=C=N—$A^2$—$R^2$, O=C=N—$A^3$—$R^7$, O=C=N—$A^4$—$R^8$, O=C=N—$A^5$—$R^9$ or O=C=N-$A^6$—R10). From a commercial viewpoint, the dehydration condensation method, particularly dehydration condensation with heating, is desirable.

The aliphatic primary amine, alicyclic primary amine or aromatic primary amine is used in an amount of about 2 to about 6 moles per mole of the BTC compound for the preparation of the bisimide of the formula (1), and in an amount of about 1 to about 3 moles per mole of the BTC compound for the preparation of the monoimide of the formula (2) or formula (3).

When it is desired to prepare an imide compound wherein groups —$A^1$—$R^1$ and —$A^2$—$R^2$, or the groups —$A^3$—$R^7$ and —$A^4$—$R^8$, or the groups —$A^5$—$R^9$ and —$A^6$—$R^{10}$ are different from each other, a mixture of primary amines having the respective groups is used in a molar ratio corresponding to the number of groups in the desired imide compound.

In the first half of the dehydration reaction, the neutralization reaction and the amidation reaction between the BTC compound and the primary amine mainly occur, and in the second half thereof, the dehydration from the amic acid formed from the BTC compound and the primary amine mainly takes place.

The dehydration reaction may be effected in the absence of a solvent or in the presence of a solvent capable of dissolving the BTC compound. Examples of useful solvents are dimethylformamide, dimethylacetamide, N-methylpyrrolidone, dimethylsulfoxide, dioxane, etc. and polar organic solvents such as lower alcohols having 1 to 4 carbon atoms, etc.

Also effective is a method which comprises reacting the BTC compound with the primary amine while dispersing them with stirring in the presence of a dispersing solvent. Examples of the dispersing solvents include aromatic hydrocarbons such as benzene, toluene, xylene, cumene, tetralin, etc., and aliphatic hydrocarbons such as pentane, hexane, heptane, nonane, decane, etc. From a commercial viewpoint, the reaction in the absence of a solvent is the most desirable, and also effective is the use of a small amount of said dispersing solvent as an entrainer.

Preferably the dehydration reaction is carried out at a temperature of 0° to about 400° C. In the first half of the reaction, any temperature in said range is employable, but in the second half thereof, a temperature of 150° to 400° C., preferably 200° to 300° C., is recommendable. At lower than 150° C., the dehydration reaction slowly proceeds and consequently it is improper as a commercial method. On the other hand, at a temperature higher than 400° C., a thermal decomposition reaction tends to occur and thus it is undesirable.

The reaction time is variable depending on the reaction temperature and cannot be specified, but is usually in the range of 1 to 50 hours.

The dehydration reaction may be conducted at atmospheric pressure or reduced pressure. It is preferred to carry out the first half of the reaction at atmospheric pressure and the second half thereof at reduced pressure. The pressure can be reduced to any level in the range of 0.01 to 760 Torr. A lower pressure of, e.g., 50 Torr or less is desirable in the last stage of the reaction.

The reaction proceeds even in the absence of a catalyst, but if desired, catalyst may be used such as hydroxides, oxides, chlorides and organic acid salts of sodium, potassium, magnesium, calcium, barium, zinc, aluminum, tin, lead and the like. Generally, reaction in the absence of such catalyst is preferable, but it is desirable to use the catalyst when the reaction is intended to produce a metal salt of the imide represented by the formula (2) or (3).

The same reaction conditions as above can be employed when an isocyanate derivative of the primary amine is used as the starting material in place of the primary amine.

The dehydration reaction may be conducted in the presence of a dehydrating agent such as acetic anhydride-pyridine, carbodiimide, triphenylphosphite, etc. In this case, the dehydrating agent is preferably used in the second half of the reaction. A preferred amount of the dehydrating agent to be used is 2 to 50 moles per mole of the BTC compound. A desirable reaction temperature is in the range of −20° to 200° C. At lower than −20° C., the reaction retards. A dehydrating agent requiring a temperature of higher than 200° C. gives only a little advantage of using such dehydrating agent and in such case the thermal dehydration reaction is preferably selected.

Aliphatic primary amines useful in said reaction include, for example, saturated or unsaturated, linear-chain or branched-chain aliphatic amines, which may have an aromatic ring. Preferred examples of aliphatic primary amines are butylamine, pentylamine, hexylamine, heptylamine, octylamine, 2-ethylhexylamine, nonylamine, decylamine, undecylamine, dodecylamine, tridecylamine, tetradecylamine, pentadecylamine, hexadecylamine, heptadecylamine, octadecylamine, nonadecylamine, eicosylamine, heneicosylamine, docosylamine, octadecenylamine, benzylamine, etc. Among them, recommendable to use are decylamine, dodecylamine, tetradecylamine, hexadecylamine, octadecylamine, etc. It is economically significant to use mixtures containing these amines substantially, namely natural material-derived amines, such as coconut oil amine, beef tallow amine, fish oil amine, hydrogenated coconut oil amine, hydrogenated beef tallow amine, hydrogenated fish oil amine, etc.

Preferred examples of alicyclic primary amines which are used in said reaction are cyclobutylamine, cyclopentylamine, cyclohexylamine, cyclohexylmethylamine, cyclohexylethylamine, methylcyclohexylamine, dimethylcyclohexylamine, etc.

Preferred examples of aromatic primary amines which are used in said reaction are butylaniline, allylaniline, pentylaniline, hexylaniline, heptylaniline, octylaniline, nonylaniline, decylaniline, undecylaniline, dodecylaniline, tridecylaniline, tetradecylaniline, pentadecylaniline, hexadecylaniline, heptadecylaniline, octadecylaniline, octadecenylaniline, nonadecylaniline, eicosylaniline, heneicosylaniline, docosylaniline, etc. Among them, more recommendable to use are decylaniline, dodecylaniline, tetradecylaniline, hexadecylaniline, octadecylaniline, etc.

The imide compounds can also be prepared by forming an intermediate partial or complete ester (tetraester) from the BTC compound and a lower alcohol of 1 to 4 carbon atoms (methyl alcohol, butyl alcohol, etc.), and then causing the amine to act on the ester. For example, to an ester formed by dissolving the BTC compound in a lower alcohol and if desired heating the solution for dehydration is added an primary amine, and then the mixture is subjected to a reaction for removing the alcohol at a temperature of 100° to 400° C., preferably 200° to 300° C., whereby the desired imide compound is produced. In this case, although the reaction is feasible at any of atmospheric pressure, reduced pressure and increased pressure, it is desirable to conduct the reaction at increased pressure (0 to 10 kg/cm$^2$G) when the primary amine has 4 to 8 carbon atoms and at reduced pressure when the primary amine has 16 or more carbon atoms.

The imide compound prepared by the foregoing method via said ester contains little or no unreacted acid component, and finds applications wherein the inclusion of acid component should be avoided to prevent the decrease of polymerization degree. For example, the compound is useful as a resin modifier for polyethyleneterephthalate (PET), polyoxymethylene (POM), polycarbonate (PC) and the like.

The desired imide compound can also be prepared by causing the amine to act on the BTC compound substantially dehydrated, e.g. by converting the BTC compound into an acid chloride by means of a chlorinating reagent such as thionyl chloride, phosgene, chlorine, phosphorus trichloride, phosphorus pentachloride, etc. The chlorinating reagent is effectively used in the second half of the reaction. When the reaction is conducted at a temperature of −20° to 200° C. in the presence of 2 to 20 moles of the chlorinating reagent per mole of the BTC compound in the second half of the reaction, the reaction is usually completed in about 1 to about 10 hours.

When the imide compound having a carboxyl group, i.e., the compound of the formula (2) or formula (3), is used among the above imide compounds, the resulting resin composition is imparted a higher affinity for a mold and an improved external lubricity. Stated more specifically, the amic acid derived from the BTC compound and the aliphatic amine is effective. For this purpose, the dehydration reaction of the BTC compound with the aliphatic amine may be controlled to leave some of carboxyl groups, when so required. In this case, the resulting imide compounds are usually obtained in the form of a mixture of the compound of the formula (2) and the compound of the formula (3).

The imide compound retaining the remaining carboxyl may be provided as such, or alternatively the imide compound may be provided in the form of a metallic soap such as soaps of sodium, potassium, magnesium, calcium, barium, zinc, aluminum, tin, lead or the like.

As a method of preparing such metallic soap, a method comprising melting the imide compound containing the remaining free carboxyl group or groups, adding to the melt a hydroxide or oxide of said metal or a solution of the hydroxide or oxide in water, methanol, ethanol or the like, and stirring the mixture is simple and therefore preferable. When the imide compound is present as dissolved in the reaction solvent of the foregoing reaction, the metallic soap can be produced in a similar manner. The stirring is effected at 50° to 130° C. and, 2 to 4 hours later, the solvent is removed by topping, whereby the desired metallic soap is obtained. The amount of the hydroxide or oxide used is preferably 0.5 to 3 moles, more preferably 1 to 2 moles, per mole of the remaining carboxyl groups. Optionally, when the reaction is performed after adding said hydroxide or oxide, the imide compound is obtained in the form of a metallic soap on termination of the reaction.

As is the case with the compound of the formula (2), the carboxyl group may be amidated with said amine to convert it into a substituted carbamoyl group. In this case, it is recommendable to add 1 to 10 moles of a primary amine per mole of the remaining carboxyl group, followed by continuing the dehydration reaction at 150° to 300° C. Usually a compound of the formula (2) having a substituted carbamoyl group is produced by the reaction for 10 minutes to 1 hour, and this compound can be used in the invention.

The imide compounds of the formula (1), (2) and (3) obtained by said techniques without a solvent can be withdrawn as such from a reaction vessel or those obtained by said techniques using a solvent, a dispersing medium or an entrainer can be withdrawn from a reaction vessel after removing the solvent, the dispersing medium or the entrainer, for example, by topping.

The obtained imide compounds of the formulas (1), (2) and (3) are solid in many cases, and is pulverized and can be added as such to the thermoplastic resin.

If a purified imide compound is required, purification can be performed by filtering off metal salts or like insolubles using a solvent, or by adsorption treatment with clay or by recrystallization, using solvents, e.g., aromatic nonpolar solvents such as benzene, toluene, xylene, etc., aliphatic polar solvents such as acetone, methyl ethyl ketone, methyl isobutyl ketone, dioxane, diglime, acetonitrile, alcohols of 1 to 4 carbon atoms, etc. and chlorine-containing solvents such as chloroform, monochlorobenzene, etc.

The chain length of alkyl or alkenyl groups represented by $R^1$, $R^2$, $R^7$, $R^8$, $R^9$ or $R^{10}$ or alkyl groups represented by $R^3$ or $R^5$ is suitably selected according to the kind of the thermoplastic resin used and the contemplated effect of the composition. Generally, the imide compound having an alkyl group or alkenyl group with a chain length of 4 to 18 carbon atoms is useful, in most cases, for reducing the melt viscosity or for promoting the crystallization. The imide compound having an alkyl group or alkenyl group with a chain length of 18 to 22 carbon atoms functions, in most cases, as an external lubricant.

The imide compounds of the present invention is usable singly or at least two of them can be used in mixture according to the desired properties. It is a matter of course that the imide compounds having the groups $-A^1-R^1$ and $-A^2-R^2$, the groups $-A^3-R^7$ and $-A^4-R^8$, or the groups $-A^5-R^9$ and $-A^6-R^{10}$ wherein the groups of each combination differ from each other can be used alone or at least two species thereof may be used in combination.

Among the foregoing imide compounds, the bisimides of the formula (1) are especially preferred. Of the bisimides of the formula (1), preferred are the compounds wherein $R^1$ and $R^2$ are the same or different and each represents an alkyl group having 4 to 22 carbon atoms, an alkenyl group having 4 to 22 carbon atoms, or a group of the formula

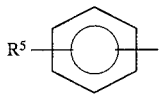

(wherein $R^5$ is an alkyl group having 4 to 22 carbon atoms), and $A^1$ and $A^2$ each represents a single bond or a phenylene group.

Further, among the bisimides of the formula (1), the compounds represented by the formula (A)

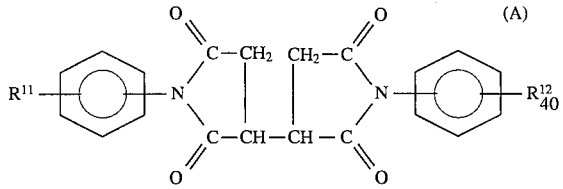

wherein $R^{11}$ and $R^{12}$ are the same or different and each represents a hydrogen atom or an alkyl group having 1 to 22 carbon atoms are novel compounds undisclosed in literature, and possess the advantages of having a high thermal decomposition temperature and being excellent in heat resistance and in compatibility with a resin depending on the kind of the resin.

The imide compounds of the formulas (1), (2) and (3) are useful as modifiers for thermoplastic resins which are required to have heat resistance. Such thermoplastic resins include, for example, polyarylene sulfides (PAS) such as polyphenylene sulfide (PPS), polysulfone, polyphenylene ether (PPE), polyether sulfone (PES), polyether ether ketone (PEEK), polyphenylene oxide (PPO), ABS modified with phenylmaleimide, α-methylstyrene and/or maleic anhydride, chlorinated polyvinyl chloride, aromatic polyamides prepared from terephthalic acid and an aliphatic diamine or from xylylenediamine and an aliphatic dicarboxylic acid, aliphatic polyamides such as 6 nylon, 6,6 nylon, 4,6 nylon, 11 nylon, 12 nylon, etc., polycarbonate (PC), polyacetal, polyethylene terephthalate (PET), polybutylene terephthalate, polyoxymethylene (POM), polyethylene naphthalene dicarboxylate (PEN), poly-1,4-cyclohexanedimethylene terephthalate, polyarylate (e.g. polyarylate prepared from bisphenol A and aromatic dicarboxylic acid comprising terephthalic acid and/or isophthalic acid, such as products commercially available under trademarks "U-Polymer" (product of Unitika Ltd.), "Arylon" (product of Du Pont), "NAP" (product of Kanegafuchi Chemical Industry Co., Ltd.)), liquid crystal polymers (e.g. liquid crystal polymers prepared from p-hydroxybenzoic acid, bisphenol and 4,4'-diphenyldicarboxylic acid as typical monomers, e.g. products commercially available under "Rodrun" (product of Unitika Ltd.), "EPE" (product of Mitsubishi Petrochemical Co., Ltd.), "Idemitsu LCP" (product of Idemitsu Petrochemical Co., Ltd.), "Ekonol" (product of Sumitomo Chemical Co., Ltd.), "Xydar" (product of Nippon Petrochemicals Co., Ltd.), "LCP" (product of Tosoh Corporation.), "Vectra" (product of Hoechst Celanease Co., Ltd.), "SRP" (product of ICI)), polyamide-imide (e.g. polyamide-imide prepared from trimellitic acid and diaminodiphenylmethane, diaminodiphenyl ether, m- or p-phenylenediamine or like aromatic diamines, etc.), polyimide, polyetherimide (e.g. products commercially available under a trade name "ULTEM" (product of General Electric Co.)), polymethylpentene, modified products of these resins, polymer alloys, etc. The foregoing imide compounds may be added to general-purpose resins other than said resins (such as polyvinyl chloride, polyethylene, polypropylene, ABS, etc.).

The foregoing modified resins and polymer alloys include, for example, mixtures of PPE/polystyrene, PPE/polyamide, PC/ABS, PC/polyester, nylon/modified polyolefin, nylon/modified ABS, nylon/polyarylate, and POM/thermoplastic polyurethane.

Useful polyimides include, for example, those comprising the repeating units of the structure represented by the formula (I) given below. Such polyimides can be prepared in the conventional manner by reacting a tetracarboxylic acid, an anhydride thereof or an ester thereof (especially $C_1$-$C_4$ alkyl ester) with a diamine or a diisocyanate.

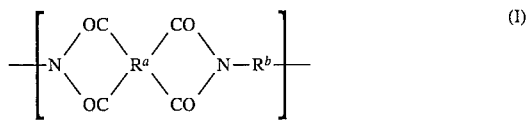

In the formula, $R^a$ is a tetravalent organic group, especially a group formed by removing 4 carboxyl groups from a tetracarboxylic acid and $R^b$ is a divalent organic group, especially a group formed by removing 2 amino groups from a diamine.

Examples of the tetracarboxylic acid are pyromellitic acid, 3,3', 4,4'-diphenylsulfonetetracarboxylic acid, 3,3', 4,4'-biphenyltetracarboxylic acid, bis(3,4-dicarboxyphenyl)ether, 3,3', 4,4'-benzophenonetetracarboxylic acid, 2,2-bis(3,4-dicarboxyphenyl)hexafluoropropane and the like. The anhydride thereof includes monoanhydrides or dianhydrides of said tetracarboxylic acids. The ester thereof includes diesters or tetraesters of said tetracarboxylic acids.

Examples of the diamine are aromatic diamines, and the specific examples are:

4,4'-diaminodiphenyl sulfide, 2,2-bis[4-(p-aminophenoxy)phenyl]propane, 2,2-bis[3-(p-aminophenoxy)phenyl]propane, 2,2-bis[4-(p-aminophenylthioether)phenyl]propane, 2,2-bis[3-(p-aminophenylthioether)phenyl]propane, 4,4'-bis(p-aminophenoxy)diphenyl sulfone, 3,3'-bis(p-aminophenoxy)diphenyl sulfone, 4,4'-bis(p-aminophenoxy)diphenyl ether, 3,3'-bis(p-aminophenoxy)diphenyl ether, 4,4'-bis(p-aminophenoxy)diphenyl sulfide,
3,3'-bis(p-aminophenoxy)diphenyl sulfide,
4,4'-bis(p-aminophenylthioether)diphenyl sulfone,
3,3'-bis(p-aminophenylthioether)diphenyl sulfone,
4,4'-bis(p-aminophenylthioether)diphenyl ether,
3,3'-bis(p-aminophenylthioether)diphenyl ether,
4,4'-bis(p-aminophenylthioether)diphenyl sulfide,
3,3'-bis(p-aminophenylthioether)diphenyl sulfide,
4,4'-bis(p-aminophenoxy)diphenyl,
3,3'-bis(p-aminophenoxy)diphenyl,
4,4'-bis(p-aminophenoxy)benzophenone,
3,3'-bis(p-aminophenoxy)benzophenone,
4,4'-bis(p-aminophenylthioether)diphenyl,
3,3'-bis(p-aminophenylthioether)diphenyl,
4,4'-bis(p-aminophenylthioether)benzophenone,
3,3'-bis(p-aminophenylthioether)benzophenone,
1,4-bis(p-aminophenylthioether)benzene,
1,3-bis(p-aminophenylthioether)benzene,
4,4'-(p-phenylenediisopropylidene)dianiline,
4,4'-(m-phenylenediisopropylidene)dianiline,
2,2-bis[4-(p-aminophenoxy)phenyl]hexafluoropropane,
4,4'-diaminodiphenyl ether,
3,4'-diaminodiphenyl ether,
3,3'-diaminodiphenyl ether,
4,4'-diaminodiphenyl sulfone,
3,4'-diaminodiphenyl sulfone,
3,3'-diaminodiphenyl sulfone,
4,4'-diaminobenzophenone,
3,3'-diaminobenzophenone,
m-phenylenediamine,
p-phenylenediamine,
3,3'-bis(3-aminophenoxy)biphenyl,
4,4'-bis(3-aminophenoxy)biphenyl,
9,10-bis(4-aminophenyl)anthracene,
9,9-bis(4-aminophenyl)fluorene, etc.

Examples of the isocyanates are diisocyanates having a structure such that the amino groups of said diamines are replaced by isocyanate groups.

The tetracarboxylic acids, anhydrides thereof or esters thereof and the diamines or diisocyanates can be used singly or in combination to the extent that the polyimide obtained has thermoplastic properties.

The melt viscosity of the thermoplastic resin to be used in the present invention is not specifically limited as far as the resin can be injection molded or blow molded. Generally, the melt viscosity is 10–100000 poise, preferably about 100–50000 poise, when determined with use of a Koka-type flow tester (300° C.; rate of shear: $10^3$/sec.).

The imide compound is used in an amount of about 0.1–100 parts by weight, preferably about 0.5–50 parts by weight, per 100 parts by weight of the thermoplastic resin. When used as viscosity-reducing agent or crystallization accelerator, the imide compound is preferably added in an amount of 1–20 parts by weight per 100 parts by weight of the thermoplastic resin. The use of less than 0.1 part by weight of the imide compound achieves little improvement in the desired properties, whereas the use of more than 100 parts by weight of the imide compound is likely to impair the heat resistance necessary to the resin.

If desired, within the range not contrary to the object of this invention, the thermoplastic resin composition of the present invention may contain, according to the intended use and purpose, a variety of additives such as a crystal nucleating agent, a reinforcing agent, a filler, an antioxidant, an ultraviolet ray absorbent, an antistatic agent, a flame retarder, etc.

When a crystal nucleating agent is used, crystallization is accelerated and this brings about better results in many cases. The amount of the crystal nucleating agent is not specifically limited. Generally, however, it is preferably used in an amount of about 0.001–10 parts by weight relative to 100 parts by weight of the thermoplastic resin. The crystal nucleating agent includes known inorganic or organic nucleating agents.

Examples of the inorganic nucleating agent are talc, mica, silica, kaolin, clay, attapulgite, romeite powder, quartz powder, zinc oxide, diatomaceous earth, montmorillonite, vermiculite, amorphous silica, glass powder, silica-alumina, wollastonite, carbon black, pyrophyllite, graphite, zinc sulfide, boron nitride, silicon resin powder, and silicates, sulfates, carbonates, phosphates, aluminates and oxides of calcium, magnesium, aluminum, lithium, barium and titanium.

Examples of the organic nucleating agent are those conventionally used in the art, e.g. aliphatic carboxylic acid metal salts, metal salts of aromatic carboxylic acids such as benzoic acid and terephthalic acid, aromatic phosphonic acids and metal salts thereof, aromatic phosphoric acid metal salts, metal salts of aromatic sulfonic acids such as benzenesulfonic acid and naphthalenesulfonic acid, metal salts of β-diketones, polymeric compound having metal salt of carboxyl groups, and fine powders of crystalline polymer such as 4,6 nylon, polyphenylenesulfide ketone, and polyester prepared using parahydroxybenzoic acid as a monomer.

A filler may be added as a reinforcing agent or as an extender. The filler is not specifically limited and may be one conventionally used in the art. Examples of the filler are carbon black, calcium carbonate, magnesium carbonate, kaolin, calcined clay, talc, aluminum silicate, calcium silicate, silicic acid, carbon fiber, glass fiber, asbestos fiber, silica fiber, zirconia fiber, aramid fiber, potassium titanate fiber, etc. The amount of the filler is not specifically limited. Generally, it is preferably used in an amount of about 10–200 parts by weight relative to 100 parts by weight of the thermoplastic resin.

The thermoplastic resin composition of the present invention can be prepared by the conventional method. For example, the desired resin composition is prepared by mixing the specified amounts of said thermoplastic resin, the imide compounds of formulas (1) to (3) and the various additives to be used as desired, by means of a V-blender, a ribbon blender, Henschel mixer, a tumble blender or the like and kneading the mixture by means of a kneading machine such as Banbury's mixer, a kneader, an oven roll, a single screw extruder, a twin-screw extruder or a single reciprocating screw at a temperature higher than the melting temperature of the resin (preferably at a temperature of the melting temperature of the resin + (about 20° to 150° C.)).

The imide compound-containing resin composition thus obtained according to the present invention is useful as molding materials for various molded articles, and can be molded by the method conventionally used in the art, e.g. by injection molding, extrusion molding, blow molding, calender molding, or rotational molding. For example, in the case of injection molding, it is preferable to employ, depending on the thermoplastic resin used, the following conditions: a resin temperature of about 200°–400° C., a mold temperature of about 0°–250° C. and an injection pressure of about 500–1300 kgf/cm². In the case of blow molding it is preferable to employ, depending on the thermoplastic resin used, the following conditions : a resin temperature of about 100°–400° C., a mold temperature of about 0°–250° C. and a blowing pressure of about 2–10 kgf/cm². The molded articles thus obtained are suitable as a material for electric and electronic appliance parts, automobile parts and chemical parts.

The resin composition containing the imide compounds of formulas (1) to (3) according to the present invention is also useful as a material for fibers, and can be made into fibers by the method conventionally used in the art. For example, the resin composition is subjected to spinning in a molten state, cooled, stretched and subjected to heat treatment, thereby giving fibers. The filaments that are spun may, after cooling, be wound as unstretched filaments, and then preheated and stretched, followed by being subjected to heat treatment under tension. Alternatively, the filaments are not wound but are drawn off by a drawn-off roll and subsequently stretched and heat-treated on a heated roller. The stretching and heat treatment are carried out in the same manner as in making conventional fibers. The preheating temperature for stretching is preferably 60°–150° C., and the temperature for heat treatment is preferably 150°–300° C. Most suitable resins for use as materials for fibers are polyethyleneterephthalate, 6-nylon, 6,6-nylon, polyarylene sulfide (PAS), etc., and in this case the reduction in the melt viscosity thereof is particularly achieved.

The thermoplastic resin composition of the present invention has the following advantages.

By adding the imide compound(s) to the thermoplastic resin according to the present invention, the melt viscosity of the resin is lowered, and in the case of crystalline resins the crystallization thereof is accelerated. Hence the thermoplastic resin composition of the invention has the advantages of increasing productivity and inhibiting thermal deterioration due to the lowered molding temperature.

When the imide compounds of the formulas (1), (2) and (3) according to the present invention are added to any of the foregoing thermoplastic resins, molding operation can be advantageously carried out to give molded articles having excellent properties.

In particular, the method of molding a thermoplastic resin according to the present invention has the advantage that the production of thin-walled molded articles or precision molding become possible and that the molding cycle can be shortened.

Particularly, in the case of PAS resin, this resin can be molded at a mold temperature of as low as 0°–100° C., and there is substantially no deterioration of the inherent properties of the resin, especially mechanical strength. Therefore, this leads to the advantage that a water cooled mold of the molding machine for general-purpose resins can be used.

When the imide compounds of formulas (1), (2) and (3) according to the present invention are blended with polyarylene sulfide (PAS) such as polyphenylene sulfide (PPS) among thermoplastic resins, more preferable results are achieved. Hereinafter, a resin composition containing polyarylene sulfide (PAS) and molding methods thereof will be described below.

The PAS to be used in the present invention is a polymer mainly containing at least 70 mole %, preferably at least 90 mole %, of a repeating unit represented by (-Ph-S-). In particular, polyphenylene sulfide (PPS) is preferably used.

There is no restriction on PPS as far as it is produced by the conventional method. For example, there can be used a comparatively low molecular weight polymer described in Japanese Unexamined Patent Publication (Kokai) No. 3368/1970, a high molecular weight polymer prepared by heating said low molecular weight polymer in an atmosphere of oxygen or by crosslinking the polymer using peroxide, and an essentially linear and comparatively high molecular weight polymer produced by the method of Japanese Unexamined Patent Publication (Kokai) No. 12240/1977.

Also usable are the PAS copolymers which contain other repeating unit as a copolymer component in an amount of more than 0 but not more than 30 mole %, preferably not more than 10 mole %.

Examples of the other repeating unit are ortho-phenylenesulfide, methaphenylenesulfide, diphenylsulfide ether, diphenylsulfide sulfone, diphenylenesulfide ketone, biphenylenesulfide, naphthalenesulfide, diphenylenesulfide methane, diphenylenesulfide propane, trifunctional phenylenesulfide, substituted phenylenesulfide (having one or two substituents selected from the group consisting of an alkyl group (particularly $C_1$–$C_4$ alkyl group), nitro group, phenyl group, a carboxylic acid group, an alkoxy group (particularly $C_1$–$C_4$ alkoxy group), amino group and the like).

The melt viscosity of the PAS or PAS copolymer is not particularly limited as far as the PAS or PAS copolymer can be injection molded. However, it is recommended that the viscosity is generally 10–100000 poise, preferably about 100–50000 poise as determined by a Koka-type flow tester (300° C.; rate of shear: $10^3$/sec.).

The imide compound is used in an amount of 0.1–100 parts by weight, preferably 0.5–50 parts by weight, relative to 100 parts by weight of the PAS or PAS copolymer. When used as a viscosity-reducing agent or crystallization accelerator, the imide compound is preferably used in an amount of 1–20 parts by weight relative to 100 parts by weight of the PAS or PAS copolymer. The use of less than 0.1 part by weight of the imide compound achieves little improvement in the desired properties, whereas the use of more than 100 parts by weight of the imide compound is likely to impair the heat resistance necessary to the resin.

If desired, the resin composition of the present invention may incorporate therein a crystal nucleating agent, a reinforcing agent, a filler, an antioxidant, an ultraviolet ray absorbent, an antistatic agent, a flame retarder, a modifier, a lubricant or the like.

When a crystal nucleating agent is used, crystallization is accelerated, and this brings about better results in many cases. The amount of the crystal nucleating agent is not specifically limited. Generally, it is preferably used in an amount of about 0.001–10 parts by weight relative to 100 parts by weight of the thermoplastic resin. The crystal nucleating agent includes known inorganic nucleating agents and organic nucleating agents.

Examples of the inorganic nucleating agent are talc, mica, silica, kaolin, clay, attapulgite, romeite powder, quartz powder, zinc oxide, diatomaceous earth, montmorillonite, vermiculite, amorphous silica, glass powder, silica-alumina, wollastonite, carbon black, pyrophyllite, graphite, zinc sulfide, boron nitride, silicon resin powder, and silicates, sulfates, carbonates, phosphates, aluminates and oxides of calcium, magnesium, aluminum, lithium, barium and titanium.

Examples of the organic nucleating agent are aliphatic carboxylic acid metal salts, metal salts of aromatic carboxylic acids such as benzoic acid and terephthalic acid, aromatic phosphonic acids and metal salts thereof, aromatic phosphoric acid metal salts, metal salts of aromatic sulfonic acids such as benzenesulfonic acid and naphthalenesulfonic acid, metal salts of β-diketones, polymeric compound having metal salt of carboxyl groups, and fine powders of crystalline polymer such as polyester prepared using parahydroxybenzoic acid as a monomer, 4,6. nylon and polyphenylenesulfide ketone.

A filler can be added as a reinforcing agent or as an extender. The filler is not specifically limited. Examples of useful fillers as reinforcing agent are carbon black, calcium carbonate, magnesium carbonate, barium sulfate, kaolin, calcined clay, talc, aluminum silicate, calcium silicate, silicic acid, carbon fiber, glass fiber, asbestos fiber, silica fiber, zirconia fiber, aramid fiber, potassium titanate fiber, and metal fiber. The amount of the filler is not specifically limited. Generally, the filler is preferably used in an amount of about 10–200 parts by weight relative to 100 parts by weight of the PAS or PAS copolymer.

In using these fillers, it is preferable to use a surface treating agent or a sizing agent if so desired. Examples of such surface treating agent and sizing agent are silane compounds epoxy compounds and isocyanate compounds.

If desired, it is also possible to add additives such as an antioxidant such as hindered amine compounds, benzophenone compounds and benzotriazole compounds, a pigment, a dye, an antistatic agent, a lubricant and a mold releasing agent.

Within the range not contrary to the object of this invention, it is possible to add other thermoplastic resin such as polyethylene, polypropylene, polybutene, polystyrene, polyphenylene ether, polyether sulfone, polyetherether ketone, polyphenylene oxide, poly-oxymethylene, PTFE, maleimide modified ABS, chlorinated PVC, aromatic polyamides prepared from terephthalic acid and an aliphatic diamine or from xylylenediamine and an aliphatic dicarboxylic acid, aliphatic polyamides such as 6 nylon, 6,6 nylon, 4,6 nylon, 11 nylon and 12 nylon, polycarbonate, polyethyleneterephthalate, polybutyleneterephthalate, polyarylate, liquid-crystal polymer, polyamide-imide, polyetherimide, polyimide, and the like.

Generally, said other thermoplastic resin is preferably used in an amount of about 10–200 parts by weight relative to 100 parts by weight of the PAS or PAS copolymer.

The PAS resin composition of the present invention can be prepared by the known method. For example, there can be mentioned a method comprising adding the imide compound of formula (1), (2) or (3) as such to PAS resin powder, a method comprising the steps of dissolving the imide compound in xylene, dimethylformamide or the like, mixing PAS resin powder with the solution and drying the mixture, a method comprising adding the imide compound to the slurry after polymerization of PAS, a method comprising homogeneously blending the imide compound and PAS resin with a reinforcing agent such as glass fiber, a filler such as calcium carbonate or other optionally usable additives by V-blender, ribbon blender, Henschel mixer, tumbler blender or the like, heating, melting and kneading the mixture using Banbury's mixer, a kneader, an oven roll, a single screw extruder, a twin-screw extruder, a single reciprocating screw or the like and pelletizing the resulting composition. The method comprising melting, kneading and pelletizing the composition is recommendable among them. In this case, it is possible to knead only the necessary components to prepare a masterbatch.

The kneading temperature is set at a temperature not lower than the melting point of the PAS resin to be used. For example, PPS resin is preferably kneaded at 280°–400° C. If the temperature is 280° C. or lower, the resin is insufficiently dissolved, whereas if the temperature is 400° C. or higher, smoke is emitted due to the decomposition of additives, hence undesirable.

The method of molding the PAS resin composition prepared by the above method can be conducted by known method.

Injection molding machine can be any of the screw-in-line type or plunger type. In order to avoid unnecessary heat history, it is preferable to use a molding machine in which the capacity of the molding machine is equal to the amount of injection. It is preferable that the screw is made of wear resistant material.

The resin pellets to be subjected to the molding are preferably pre-dried at 120°–160° C. for 2 to 6 hours, whereby insufficient appearance such as silver streak, haze or the like is unlikely to occur.

The resin temperature in injection molding is preferably 280°–400° C., in particular about 290°–360° C.

The mold temperature is generally 0°–100° C., and particularly 40°–80° C. is recommended. However, it is also possible to conduct injection molding at a mold temperature of 100° C. or higher (e.g., about 130° C.). When the heat resistance of the molded article is important, a high mold temperature is preferable and gives better results, whereas when dimensional accuracy is considered to be important, a low mold temperature brings about better results.

The injection pressure is preferably 500–1300 kg/cm$^2$. Generally, molded articles having uniform and lustrous surface are obtained when the injection is conducted at a high pressure and a high speed, whereas molded articles having less warping and flash are obtained when the injection is carried out at a low pressure and a low speed.

The rotation speed of the screw is 10–300 rpm, preferably about 40–200 rpm.

When the molding cycle is desired to be quickened, it is preferable to increase the rotation speed. However, excessive increase in rotational frequency is unfavorable because it causes severance of glass fiber and generation of heat from the resin.

The PAS resin composition according to the present invention has a high crystallization speed, can be molded at a mold temperature ranging from low to high temperature, and the molded articles obtained have good appearance and few flash and are low in dimension shrinkage percentage and excellent in mechanical strength. Therefore, the composition is suitable for molding materials for various molded articles such as electric and electronic appliance parts, automobile parts and chemical parts.

The present invention will be described in greater detail with reference to Production Examples which illustrate the preparation of the imide compounds or PPS resin and Examples which illustrate the resin compositions prepared by incorporating the imide compounds into thermoplastic resins.

The imide compounds prepared in Production Examples were identified by NMR and IR analyses.

PRODUCTION EXAMPLE 1

A 19.8 g quantity (0.1 mole) of BTC dianhydride and 53.8 g (0.2 mole) of stearylamine were mixed with stirring in 500 ml of xylene and the temperature was raised to 130° C. While water that generated and xylene were removed and separated by cooling a distilled water-xylene azeotropic mixture by means of a cooler, the reaction mixture was heated until the reaction temperature reached 260° C. The reaction was continued until 3.6 g of the generated water was removed from the reaction system. After completion of the reaction, the reaction mixture was neutralized with a 10% aqueous solution of sodium hydroxide, treated with clay and filtered, and the remaining xylene was removed by topping, thus giving the desired imide compound (imide A).

Said imide A is a bisimide of the formula (1) wherein $R^1$ and $R^2$ each represent a $C_{18}$ alkyl group and $A^1$ and $A^2$ each represent a single bond.

PRODUCTION EXAMPLE 2

The same procedure as in Preparation Example 1 was repeated using 23.4 g (0.1 mole) of BTC, 51.8 g (0.2 mole) of tallow amine and 500 ml of xylene. The reaction was terminated when 6.6 g of the generated water was distilled off. After completion of the reaction, and the remaining xylene was removed by topping, thus giving the desired imide compound (imide B) having a residual carboxyl group.

This imide B is a mixture which comprises, as a main component, a bisimide of the formula (1) wherein $R^1$ and $R^2$ each represent a $C_8$–$C_{22}$ alkyl or alkenyl group and $A^1$ and $A^2$ each represent a single bond, and which further comprises a monoimide of the formula (2) wherein $R^7$ represents a $C_8$–$C_{22}$ alkyl or alkenyl group, $A^3$ represents a single bond, X represents —NH—$R^8$ (wherein $R^8$ represents a $C_8$–$C_{22}$ alkyl or alkenyl group) and Y represents —OH, and a monoimide of the formula (3) wherein $R^9$ and $R^{10}$ each represent a $C_8$–$C_{22}$ alkyl or alkenyl group and $A^5$ and $A^6$ each represent a single bond.

PRODUCTION EXAMPLE 3

The same procedure as in Preparation Example 1 was repeated using 23.4 g (0.1 mole) of BTC, 51.8 g (0.2 mole) of tallow amine and 500 ml of xylene. The reaction was terminated when 6.6 g of the generated water was distilled off. After completion of the reaction, the reaction mixture was neutralized with addition of 1.2 g of calcium hydroxide, and the remaining xylene was removed by topping, thus giving the desired imide compound (imide C) containing a carboxylic acid calcium salt.

This imide C is a mixture which comprises, as a main component, a bisimide of the formula (1) wherein $R^1$ and $R^2$ each represent a $C_8$–$C_{22}$ alkyl or alkenyl group and $A^1$ and $A^2$ each represent a single bond, and which further comprises a calcium salt of a monoimide of the formula (2) wherein $R^7$ represents a $C_8$–$C_{22}$ alkyl or alkenyl group, $A^3$ represents a single bond, X represents —NH—$R^8$ (wherein $R^8$ represents a $C_8$–$C_{22}$ alkyl or alkenyl group) and Y represents —OH, and a calcium salt of a monoimide of the formula (3) wherein $R^9$ and $R^{10}$ each represent a $C_8$–$C_{22}$ alkyl or alkenyl group and $A^5$ and $A^6$ each represent a single bond.

PRODUCTION EXAMPLE 4

The same procedure as in Preparation Example 1 was repeated using 23.4 g (0.1 mole) of BTC, 52.2 g (0.2 mole) of p-dodecylaniline and 500 ml of xylene. The reaction was terminated when 6.6 g of the formed water was distilled off. After completion of the reaction, the reaction mixture was neutralized with a 10% aqueous solution of potassium hydroxide, treated with clay and filtered, and the remaining xylene was removed by topping, thus giving the desired imide compound (imide D).

This imide D is a mixture which comprises, as a main component, a bisimide of the formula (1) wherein $R^1$ and $R^2$ each represent a $C_{12}$ alkyl group and $A^1$ and $A^2$ each represent a phenylene group, and which further comprises a monoimide of the formula (2) wherein $R^7$ represents a $C_{12}$ alkyl group, $A^3$ represents a phenylene group, X represents a group —NH—$A^4$—$R^8$ (wherein $A^4$ represents a phenylene group, $R^8$ represents a $C_{12}$ alkyl group) and Y represents —OH, and a monoimide of the formula (3) wherein $R^9$ and $R^{10}$ each represent a $C_{12}$ alkyl group and $A^5$ and $A^6$ each represent a phenylene group.

PRODUCTION EXAMPLE 5

The same procedure as in Preparation Example 1 was repeated using 20.4 g (0.1 mole) of BTC monoanhydride, 41.0 g (0.2 mole) of p-butylaniline and 500 ml of xylene. The reaction was terminated when 3.3 g of the formed water was distilled off. After completion of the reaction, and the remaining xylene was removed by topping, thus giving the desired imide compound (imide E) having a residual carboxylic group.

This imide E is a mixture which comprises, as a main component, a bisimide of the formula (1) wherein $R^1$ and $R^2$ each represent a $C_4$ alkyl group and $A^1$ and $A^2$ each represent a phenylene group, and which further comprises a monoimide of the formula (2) wherein $R^7$ represents a $C_4$ alkyl group, represents a phenylene group, X represents a group —NH—$A^4$—$R^8$ (wherein $A^4$ represents a phenylene group, $R^8$ represents a $C_4$ alkyl group) and Y represents —OH, and a monoimide of the formula (3) wherein $R^9$ and $R^{10}$ each represent a $C_4$ alkyl group and $A^5$ and $A^6$ each represent a phenylene group.

PRODUCTION EXAMPLE 6

The same procedure as in Preparation Example 1 was repeated using 19.8 g (0.1 mole) of BTC dianhydride, 46.6 g (0.2 mole) of p-decylaniline and 500 ml of xylene. The reaction was terminated when 3.3 g of the formed water was distilled off. After completion of the reaction, the reaction mixture was neutralized with calcium hydroxide and the remaining xylene was removed by topping, thus giving the desired imide compound (imide F) containing a carboxylic acid salt.

This imide F is a mixture which comprises, as a main component, a bisimide of the formula (1) wherein $R^1$ and $R^2$ each represent a $C_{10}$ alkyl group and $A^1$ and $A^2$ each represent a phenylene group, and which further comprises a calcium salt of a monoimide of the formula (2) wherein $R^7$ represents a $C_{10}$ alkyl group, $A^3$ represents a phenylene group, X represents a group —NH—$A^4$—$R^8$ (wherein $A^4$ represents a phenylene group and $R^8$ represents a $C_{10}$ alkyl group) and Y represents —OH, and a calcium salt of a monoimide of the formula (3) wherein $R^9$ and $R^{10}$ each represent a $C_{10}$ alkyl group and $A^5$ and $A^6$ each represent a phenylene group.

EXAMPLE 1

Five parts by weight of "imide A" was added to 100 parts by weight of PET resin, and the mixture was melted and mixed at 260° C. in an extruder. The extruded strand was cooled with water and cut to prepare a specimen.

The melt flow index (MFI) of the specimen was determined as the amount of molten resin extruded from an orifice (2 mm in diameter, 8 mm in length) for 10 minutes at a temperature of 275° C. and under a load of 2 kg. The obtained value was 31 cm³/10 min.

COMPARATIVE EXAMPLE 1

The MFI of the PET resin per se used in Example 1 was determined following the procedure of Example 1. The obtained value was 18 cm³/10 min.

EXAMPLE 2

One hundred parts by weight of PET resin, 5 parts by weight of "imide C" and 3 parts by weight of talc as a crystallization nucleating agent were mixed at 50° C. with a Henschel mixer. The mixture was then melted and mixed at 260° C. in an extruder, and the extruded strand was cooled with water and cut to prepare a specimen.

Fifteen mg of the specimen was placed in a differential scanning calorimeter (DSC), heated at a rate of 10° C./min., melted at 300° C. for 3 minutes and cooled at a rate of 10° C./min. The difference ($\Delta t$) between the crystallization temperature measured during heating and the melting point measured during cooling (crystallization temperature measured during cooling) was 124° C., and the crystallization temperature was 84° C.

The difference ($\Delta t$) between the crystallization temperature measured during heating and the melting point measured during cooling (crystallization temperature measured during cooling) is an index of the crystallization rate. The greater the difference, the higher the crystallization rate of the resin composition.

Further, the lower crystallization temperature is indicative of the promoted crystallization of the resin composition.

COMPARATIVE EXAMPLE 2

The difference in crystallization temperatures ($\Delta t$) of the PET resin per se used in Example 2 was determined following the procedure of Example 2. The obtained value was 90° C. and the crystallization temperature was 117° C.

EXAMPLE 3

One hundred parts by weight of 12 nylon resin and 5 parts by weight of "imide B" were kneaded on an oven roll at 180° C. to prepare a specimen.

The MFI of the specimen was determined as the amount of molten resin extruded from an orifice having a diameter of 1 mm and the length of 10 mm for 10 minutes at a temperature of 240° C. under a load of 20 kg. The obtained value was 12.4 cm³/10 min.

COMPARATIVE EXAMPLE 3

The MFI of the nylon resin per se used in Example 3 was determined following the procedure of Example 3. The obtained value was 5.6 cm³/10 min.

EXAMPLE 4

One hundred parts by weight of PPS resin and 5 parts by weight of "imide A" were melted, mixed and kneaded at 290° C. with a labo plastomixer to prepare a specimen.

According to the DSC measurement (conditions: sample 15 mg, heated at a rate of 10° C./min., melted at 330° C. for 3 minutes and cooled at a rate of 10° C./min), the temperature difference ($\Delta t$) was 165° C. and the crystallization temperature was 117° C.

EXAMPLE 5

A specimen was prepared in the same manner as in Example 4 with the exception of using 5 parts by weight of "imide F".

According to the DSC measurement (conditions: the same as in Example 4), the temperature difference ($\Delta t$) was 175° C. and the crystallization temperature was 109° C.

COMPARATIVE EXAMPLE 4

The temperature difference ($\Delta t$) of the PPS resin per se used in Example 4 was determined following the procedure of Example 4. The obtained value was 156° C. and the crystallization temperature was 128° C.

EXAMPLE 6

One hundred parts by weight of chlorinated vinyl chloride resin with a chlorination degree of about 65%, 5 parts by weight of "imide B", 1.5 parts by weight of dibutyltin maleate, 1.5 parts by weight of dibutyltin sulfide, 0.4% of butyl stearate and 0.4% of stearyl alcohol were mixed using a Henschel mixer, and the mixture was melted and mixed on a roll at 190° C. to prepare a specimen.

The MFI of the specimen was determined as the amount of the molten resin extruded from an orifice having a diameter of 1 mm and a length of 10 mm for 10 minutes at a temperature of 190° C. under a load of 160 kg. The obtained value was 520 cm³/10 min.

COMPARATIVE EXAMPLE 5

The MFI of a chlorinated vinyl chloride resin composition was determined following the procedure of Example 6, the resin composition having the same formulation as the one used in Example 6 with the exception that "imide B" was not added. The obtained value was 270 cm³/10 min.

EXAMPLE 7

Five parts by weight of "imide D" was dry-blended with 100 parts by weight of POM resin. The mixture was melted and kneaded at 230° C. in a twin-screw extruder and extruded into water and cut to prepare a specimen.

The MFI (190° C., under a load of 2.19 kg) of this specimen was determined, and the obtained value was 15.8 cm³/10 min.

COMPARATIVE EXAMPLE 6

The MFI of the POM resin per se used in Example 7 was determined following the procedure of Example 7. The obtained value was 7.0 cm³/10 min.

EXAMPLE 8

Two parts by weight of "imide E" was thoroughly mixed with 100 parts by weight of ABS resin with a Henschel mixer, and the mixture was kneaded in a single-screw extruder to prepare pellets.

The flow length of the pellets was determined at 260° C. by means of an injection molding machine using a spiral mold. The obtained value was 63.5 cm.

Longer flow length is indicative of lower melt viscosity of the resin composition.

COMPARATIVE EXAMPLE 7

The flow length of the ABS resin per se used in Example 8 was determined following the procedure of Example 8. The obtained value was 47.9 cm.

EXAMPLE 9

Two parts by weight of "imide A" was added to 100 parts by weight of powdery thermoplastic polyimide obtained by dehydration condensation of 3,3', 4,4'-diphenylsulfontetracarboxylic acid dianhydride and 2,2-bis[4-p-aminophenoxy)phenyl]propane at 170° C., and the mixture was mixed by means of an extruder until-it became homogeneous. The extruded strand was cooled with water and cut to prepare a specimen.

Subsequently, according to JIS K7210 (flow test method (reference test)), the melt viscosity of the specimen at 360° C. was determined (apparatus: "CFT-500C" manufactured by Shimadzu Seisakusho Ltd., test pressure: 100 kgf/cm$^2$, die: 1×10 mm). As a result, the melt viscosity of the specimen was found to be 20,600 poise.

The melt viscosity of the above powdery thermoplastic polyimide per se, as determined in the same manner as above, was 68,000 poise.

Therefore, it was observed that addition of imide A of the present invention results in a remarkable decrease in melt viscosity.

Further, neither void nor coloring due to decomposition were recognized on the obtained strands.

As apparent from the Examples and Comparative Examples, addition of the imide compound of the present invention to a thermoplastic resin can decrease the melt viscosity of the resin, and promote the crystallization of the resin if the resin is crystalline.

A resin composition prepared by adding the imide compound of the present invention to polyphenylene sulfide (PPS) is illustrated below.

PRODUCTION EXAMPLE 7

A 650 g (5.0 moles), quantity of sodium sulfide·2.9 hydrate and 1800 g of N-methylpyrrolidone (NMP) were placed in an autoclave. The mixture was heated to 205° C., and about 150 g of distilled water was removed therefrom. Subsequently, 720 g (4.85 moles) of p-dichlorobenzene and 400 g of N-methylpyrrolidone (NMP) were added and a reaction was carried out at 250° C. for 4 hours.

After completion of the reaction, the reaction mixture was cooled to room temperature and filtered to collect the product. The product was repeatedly washed with warm water and dried at 100° C. for twenty four hours to obtain a PPS resin (PPS-1) having a melt viscosity of 300 poise (determined with a Koka type flow tester, the same applies hereinafter).

PRODUCTION EXAMPLE 8

"PPS-1" was thermally crosslinked by subjecting the resin to heat treatment in the air at 260° C. for 5 hours, giving a PPS resin (PPS-2) having a melt viscosity of 2500 poise.

PRODUCTION EXAMPLE 9

A 650 g (5.0 moles) quantity of sodium sulfide·2.9 hydrate, 210 g (5.0 moles) of lithium chloride and 1800 g of MNP were placed in an autoclave and the mixture was heated to 205° C. to remove about 140 g of the water that was distilled. Subsequently, 720 g (4.85 moles) of p-dichlorobenzene and 400 g of NMP were added and a reaction was carried out at 250° C. for 4 hours.

On completion of the reaction, the reaction mixture was cooled to room temperature and filtered to collect the product. The product was repeatedly washed with warm water and dried at 100° C. for twenty four hours to obtain a PPS resin (PPS-3) having a melt viscosity of 1800 poise.

PRODUCTION EXAMPLE 10

A 19.8 g (0.1 mole) of BTC dianhydride and 53.8 g (0.2 mole) of tallow amine were mixed and stirred in 500 ml of xylene and heated to 130° C. The mixture was further heated to the final temperature of 260° C. while separating and removing the generated water and xylene by cooling the distilled xylene-water azeotropic mixture with a condenser. The reaction was continued until 3.6 g of the generated water was removed from the reaction system.

On completion of the reaction, the reaction mixture was neutralized with an aqueous solution of potassium hydroxide, treated with clay and filtered, and the remaining xylene was removed by topping. Thus, an imide compound (imide G) was obtained.

This imide G is a bisimide represented by the formula (1) wherein $R^1$ and $R^2$ each represent $C_8$–$C_{22}$ alkyl or alkenyl group and $A^1$ and $A^2$ each represent a single bond.

PRODUCTION EXAMPLE 11

The procedure of Production Example 10 was repeated using 19.8 g (0.1 mole) of BTC dianhydride, 34.0 g (0.2 mole) of laurylamine and xylene, and the reaction was completed when 3.0 g of the generated water was distilled off. On completion of the reaction, the reaction mixture as such was subjected to topping to remove xylene. Thus, a monoimide compound (imide H) was obtained wherein the carboxyl groups partially remained.

This imide H is a mixture which comprises, as the main component, a bisimide of the formula (1) wherein $R^1$ and $R^2$ each represent a $C_{12}$ alkyl group and $A^1$ and $A^2$ each represent a single bond, and which further comprises a monoimide of the formula (2) wherein $R^7$ is a $C_{12}$ alkyl group, $A^3$ is a single bond, X is a group —NH—$A^4$—$R^8$ (wherein $A^4$ is a single bond and $R^8$ is a $C_{12}$ alkyl group) and Y is —OH, and a monoimide of the formula (3) wherein $R^9$ and $R^{10}$ each represent a $C_{12}$ alkyl group and $A^5$ and $A^6$ each represent a single bond.

PRODUCTION EXAMPLE 12

The procedure of Production Example 10 was repeated using 23.4 g (0.1 mole) of BTC, 34.0 g (0.2 mole) of laurylamine and xylene, and the reaction was terminated when 5.4 g of the generated water was distilled off. On completion of the reaction, the reaction mixture was neutralized with sodium hydroxide and the neutralized mixture as such was subjected to topping to remove xylene. Thus, an imide compound (imide I) containing carboxylic acid sodium salt was obtained.

This imide I is a mixture which comprises, as the main component, a bisimide of the formula (1) wherein $R^1$ and $R^2$ each represent a $C_{12}$ alkyl group and $A^1$ and $A^2$ each represent a single bond, and which further comprises a sodium salt of a monoimide of the formula (2) wherein $R^7$ is a $C_{12}$ alkyl group, $A^3$ is a single bond, X is a group $-NH-A^4-R^8$ (wherein $A^4$ is a single bond and $R^8$ is a $C_{12}$ alkyl group) and Y is $-OH$, and a sodium salt of a monoimide of the formula (3) wherein $R^9$ and $R^{10}$ each represent a $C_{12}$ alkyl group and $A^5$ and $A^6$ each represent a single bond.

PRODUCTION EXAMPLE 13

The procedure of Production Example 10 was repeated using 23.4 g (0.1 mole) of BTC, 52.2 g (0.2 mole) of paradodecylaniline and xylene, and the reaction was terminated when 7.2 g of the generated water was distilled off. After completion of the reaction, the reaction mixture was neutralized with calcium hydroxide and the neutralized mixture as such was subjected to topping to remove xylene. Thus, an imide compound (imide J) was obtained.

Imide J is a mixture which comprises, as the main component, a bisimide of the formula (1) wherein $R^1$ and $R^2$ each represent a $C_{12}$ alkyl group and $A^1$ and $A^2$ each represent a phenylene group, and which further comprises a calcium salt of a monoimide of the formula (2) wherein $R^7$ is a $C_{12}$ alkyl group, $A^3$ is a phenylene group, X is a group $-NH-A^4-R^8$ (wherein $A^4$ is a phenylene group and $R^8$ is a $C_{12}$ alkyl group) and Y is $-OH$, and a calcium salt of a monoimide of the formula (3) wherein $R^9$ and $R^{10}$ each represent a $C_{12}$ alkyl group and $A^5$ and $A^6$ each represent a phenylene group.

EXAMPLES 10–14

A PPS resin, an imide compound and, where necessary, talc as shown in the following Table 1 were preliminarily mixed using a Henschel mixer, and 65 parts by weight of a commercially available glass fiber was added to 100 parts by weight of the PPS resin. The mixture thus obtained was melted and kneaded in an extruder having a cylinder temperature of 310° C. to obtain pellets of a PPS resin composition. The pellets were then injection-molded at a cylinder temperature of 310° C. and a mold temperature of 70° C.

The tensile strength, flexural strength and Izod impact strength of the thus-obtained test pieces were respectively determined by the following methods.

(a) Tensile strength

Determined based on ASTM-D68.

(b) Flexural strength of the molded product

Determined based on ASTM-D790.

(c) Izod impact strength of the molded product

Determined based on ASTM-D256

The obtained results are shown in Table 1.

COMPARATIVE EXAMPLE 8

The tensile strength, flexural strength and Izod impact strength of a molded product prepared from PPS-1 alone were determined. The obtained results are shown in Table 1.

COMPARATIVE EXAMPLE 9

A PPS resin composition was prepared in the same manner as in Example 11 with the exception of using ethylenebisstearamide (EBS) in lieu of "imide H". The tensile strength, flexural strength and Izod impact strength of the molded product of the composition were determined. The obtained results are shown in Table 1.

COMPARATIVE EXAMPLE 10

A PPS resin composition was prepared in the same manner as in Example 12 except that "imide G" was not used. The tensile strength, flexural strength and Izod impact strength of the molded product of the composition were determined. The obtained results are shown in Table 1.

As apparent from Table 1, according to the method of the present invention, molding can be conducted even at a low temperature without impairing the inherent mechanical properties and heat resistance of polyarylene sulfide.

TABLE 1

|  | Examples | | | | | Comp. Ex | | |
| --- | --- | --- | --- | --- | --- | --- | --- | --- |
|  | 10 | 11 | 12 | 13 | 14 | 8 | 9 | 10 |
| PPS resin | | | | | | | | |
| PPS-1 | 100 | | | | | 100 | | |
| PPS-2 | | 100 | | | | | 100 | |
| PPS-3 | | | 100 | 100 | 100 | | | 100 |
| Imide compound | | | | | | | | |
| Present imide G | 3 | | 3 | | | | | |
| Present imide H | | 3 | | | | | | |
| Present imide I | | | | 3 | | | | |
| Present imide J | | | | | 5 | | | |
| Resin reforming agent | | | | | | | | |
| Talc | | | 3 | | | | | 3 |
| EBS | | | | | | | 3 | |
| Tensile strength (kg/cm$^2$) | 1350 | 1750 | 1790 | 1750 | 1780 | 1180 | 1680 | 1670 |
| Flexural strength (kg/cm$^2$) | 1900 | 2440 | 2480 | 2450 | 2480 | 1760 | 2320 | 2320 |
| Izod impact strength (kg.cm/cm) | 8.6 | 9.8 | 14.5 | 12.8 | 14.2 | 4.8 | 6.5 | 9.9 |

PRODUCTION EXAMPLE 14

A 23.4 g quantity (0.1 mole) of BTC and 52.2 g (0.2 mole) of p-dodecylaniline were mixed and stirred in 500 ml of xylene. The mixture was heated until the reaction temperature finally reached 260° C., while removing and separating the generated water and xylene by cooling the distilled xylene-water azeotropic mixture with a condenser. The reaction was continued until 6.9 g of water was separated and removed from the reaction system.

For purification by recrystallization, after the reaction, the reaction mixture was dissolved in 250 g of toluene/methyl ethyl ketone/dimethylformamide solvent mixture (weight ratio: 3/1/1) with heating. Then, 3 g of calcium oxide was added, dispersed and stirred. The dispersion was filtered to remove insoluble matters. The filtrate was cooled to obtain 41 g of a bisimide of BTC and p-dodecylaniline.

The obtained compound was a solid having a melting point of 203° C.

The characteristic absorption of the infrared absorption was as follows.

υ (C=)) 1778, 1703 cm$^{-1}$ (characteristic absorption of imido group)

The structure of the obtained bisimide

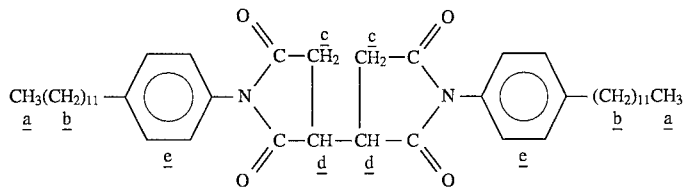

The results of elementary analysis were as follows.

|  | C | H | O | N |
|---|---|---|---|---|
| Found (%) | 77.5 | 9.4 | 9.1 | 4.0 |
| Calcd. (%) | 77.2 | 9.4 | 9.3 | 4.1 |

We claim:

1. A thermoplastic resin composition characterized in that it comprises a thermoplastic resin and 0.1 to 100 parts by weight, per 100 parts by weight of said thermoplastic resin, of an imide compound, said imide compound being at least one member selected from the group consisting of:

(1) a bisimide represented by the formula

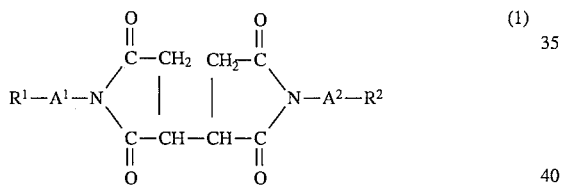

wherein $R^1$ and $R^2$ are the same or different and each represents an alkyl or alkenyl group having 4 to 22 carbon atoms, a cycloalkyl group having 4 to 6 carbon atoms, a group represented by the formula

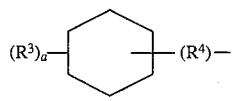

or a group represented by the formula

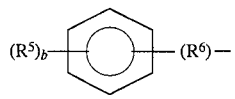

in which $R^3$ and $R^5$ are the same or different and each represents an alkyl group having 1 to 22 carbon atoms, $R^4$ and $R^6$ are the same or different and each represents a single bond or an alkylene group having 1 to 2 carbon atoms, a is an integer of 1 to 2 and b is an integer of 0 to 2, and $A^1$ and $A^2$ are the same or different and each represents a single bond or a phenylene group;

(2) a monoimide represented by the formula

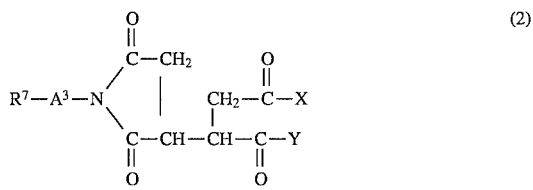

wherein X and Y are the same or different and each represents a group —NH—$A^4$—$R^8$ or a hydroxyl group, $R^7$ and $R^8$ have the same meaning as $R^1$ in the formula (1) and may be the same or different, and $A^3$ and $A^4$ are the same or different and each represents a single bond or a phenylene group, and a metal salt thereof; and (3) a monoimide represented by the formula

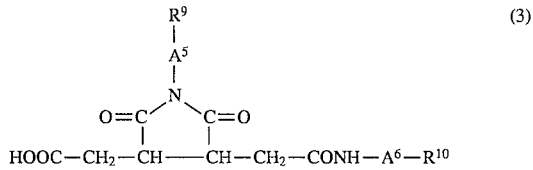

wherein $R^9$ and $R^{10}$ are the same or different and each represents an alkyl or alkenyl group having 4 to 22 carbon atoms, and $A^5$ and $A^6$ are the same or different and each represents a single bond or a phenylene group, and a metal salt thereof.

2. A thermoplastic resin composition according to claim 1 wherein the thermoplastic resin is a resin selected from the group consisting of polyphenylene sulfide (PPS), polysulfone, polyphenylene ether (PPE), polyether sulfone (PES), polyether ether ketone (PEEK), polyphenylene oxide (PPO), ABS modified with phenylmaleimide, α-methylstyrene and/ or maleic anhydride, chlorinated polyvinyl chloride, aromatic polyamides prepared from terephthalic acid and an aliphatic diamine or from xylylenediamine and an aliphatic dicarboxylic acid, aliphatic polyamide such as 6 nylon, 6,6 nylon, 4,6 nylon, 11 nylon or 12 nylon, polycarbonate (PC), polyacetal, polyethylene terephthalate (PET), polybutylene terephthalate, polyoxymethylene (POM), polyethylene naphthalene dicarboxylate (PEN), poly-1,4-cyclohexane-dimethylene terephthalate, polyarylate, liquid crystal polymers, polyamide-imide, polyimide, polyetherimide, polymethyl pentene, modified products of these resins, polymer alloys, polyvinyl chloride, polyethylene, polypropylene and ABS.

3. A thermoplastic resin composition according to claim 1 wherein the thermoplastic resin is a polyarylene sulfide (PAS) resin.

4. A thermoplastic resin composition according to claim 1 wherein the thermoplastic resin is a PAS copolymer containing a repeating unit represented by the formula (-Ph-S-) in an amount of not less than 70 mole % but less than 100 mole % and other repeating unit as a copolymerized component in an amount of 30 mole % or less.

5. A thermoplastic resin composition according to claim 1 wherein the thermoplastic resin is a PAS copolymer containing a repeating unit represented by the formula (-Ph-S-) in an amount of not less than 90 mole % but less than 100 mole % and other repeating unit as a copolymerized component in an amount of 10 mole % or less.

6. A thermoplastic resin composition according to claim 1 wherein the thermoplastic resin is polyphenylene sulfide (PPS).

7. A thermoplastic resin composition according to claim 3 wherein the polyarylene sulfide (PAS) resin has a melt viscosity of about 10 to about 100,000 poises (300° C., shear rate of $10^3$/sec) as determined by a Koka-type flow tester.

8. A thermoplastic resin composition according to claim 3 wherein the polyarylene sulfide (PAS) resin has a melt viscosity of about 100 to about 50,000 poises (300° C., shear rate of $10^3$/sec) as determined by a Koka-type flow tester.

9. A thermoplastic resin composition according to claim 1 wherein the imide compound is a bisimide represented the formula (1).

10. A thermoplastic resin composition according to claim 1 wherein the imide compound is a bisimide represented by the formula (1) wherein $R^1$ and $R^2$ are the same or different and each represents an alkyl group having 4 to 22 carbon atoms, an alkenyl group having 4 to 22 carbon atoms, or a group of the formula

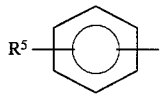

(wherein $R^5$ is an alkyl group having 4 to 22 carbon atoms), and $A^1$ and $A^2$ each represent a single bond or a phenylene group.

11. A thermoplastic resin composition according to claim 1 wherein the imide compound is used in an amount of about 0.5 to about 50 parts by weight per 100 parts by weight of the thermoplastic resin.

12. A thermoplastic resin composition according to claim 1 which further contains at least one member selected from a nucleating agent and a filler.

13. A method of molding a thermoplastic resin composition, characterized in that the method comprises injection-molding or blow-molding a resin composition comprising a thermoplastic resin and 0.1 to 100 parts by weight, per 100 parts by weight of said thermoplastic resin, of at least one imide compound selected from the group consisting of the bisimide of the formula (1), the monoimide of the formula (2) and a metal salt thereof and the monoimide of the formula (3) and a metal salt thereof, all as defined in claim 1.

14. A method according to claim 13 wherein the thermoplastic resin is polyarylene sulfide (PAS) resin.

15. A method according to claim 14 wherein the polyarylene sulfide (PAS) resin is a copolymer containing a repeating unit represented by the formula (-Ph-S-) in an amount of not less than 70 mole % but less than 100 mole % and other repeating unit as a copolymerized component in an amount of more than 0 mole % but not more than 30 mole %.

16. A method according to claim 14 wherein the polyarylene sulfide (PAS) resin is a copolymer containing a repeating unit represented by the formula (-Ph-S-) in an amount of not less than 90 mole % but less than 100 mole % and other repeating unit as a copolymerized component in an amount of more than 0 mole % but not more than 10 mole %.

17. A method according to claim 14 wherein the polyarylene sulfide (PAS) resin is polyphenylene sulfide (PPS).

18. A method according to claim 14 wherein the polyarylene sulfide (PAS) resin has a melt viscosity of about 10 to about 100,000 poises (300° C., shear rate of $10^3$/sec) as determined by a Koka-type flow tester.

19. A method according to claim 14 wherein the polyarylene sulfide (PAS) resin has a melt viscosity of about 100 to about 50,000 poises (300° C., shear rate of $10^3$/sec) as determined by a Koka-type flow tester.

20. A method according to claim 13 wherein the imide compound is a bisimide represented by the formula (1).

21. A method according to claim 13 wherein the imide compound is a compound represented by the formula (1) wherein $R^1$ and $R^2$ are the same or different and each represents an alkyl group having 4 to 22 carbon atoms, an alkenyl group having 4 to 22 carbon atoms, or a group of the formula

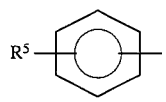

(wherein $R^5$ is an alkyl group having 4 to 22 carbon atoms), and $A^1$ and $A^2$ each represent a single bond or a phenylene group.

22. A method according to claim 13 wherein the imide compound is used in an amount of about 0.5 to about 50 parts by weight per 100 parts by weight of the thermoplastic resin.

23. A method according to claim 13 wherein the resin composition contains at least one member selected from a nucleating agent, a filler and other thermoplastic resin.

24. A method according to claim 13 wherein the resin composition is injection-molded under the conditions: a resin temperature of 200° to 400° C., a mold temperature of 0° to 250° C., and an injection pressure of 500 to 1300 kg/cm².

25. A method according to claim 14 wherein the injection-molding is effected at a mold temperature of 0° to 100° C.

26. A method according to claim 14 wherein the PAS resin composition is injection-molded under the conditions: a resin temperature of 280° to 400° C., a mold temperature of 0° to 100° C., and an injection pressure of 500 to 1300 kg/cm².

\* \* \* \* \*